United States Patent [19]
Davis

[11] Patent Number: 4,763,441
[45] Date of Patent: Aug. 16, 1988

[54] PROCESS FOR FORMING SUBSTANTIALLY UNIFORM SEED ASSEMBLAGES CAPABLE OF GROWING $F_1$ HYBRID AND RESTORER SOYBEAN PLANTS

[75] Inventor: William H. Davis, Plainview, Tex.

[73] Assignee: Ring Around Products, Inc., Prattville, Ala.

[21] Appl. No.: 54,767

[22] Filed: May 27, 1987

[51] Int. Cl.$^4$ ............................................. A01H 1/02
[52] U.S. Cl. .................................... 47/58; 47/DIG. 1
[58] Field of Search .................. 47/58, DIG. 1; 800/1

[56] References Cited

U.S. PATENT DOCUMENTS

| | | | |
|---|---|---|---|
| 3,842,538 | 10/1974 | Barabas | 47/58 |
| 3,903,645 | 9/1975 | Bradner | 47/58 |
| 4,077,157 | 5/1978 | Bradner | 47/58 |
| 4,545,146 | 10/1985 | Davis | 47/58 |
| 4,648,204 | 5/1987 | Davis | 47/58 |

*Primary Examiner*—Robert E. Bagwill
*Attorney, Agent, or Firm*—Burns, Doane, Swecker & Mathis

[57] ABSTRACT

An efficient process employing cytoplasmic male sterility is provided wherein seeds capable of forming $F_1$ hybrid *Glycine max* plants and restorer plants for the same simultaneously are formed in bulk in a single planting area and the seed harvest subsequently is segregated to form two substantially uniform seed assemblages. The parent soybean plants are provided with distinctly colored maternally-derived seedcoats wherein the genes for seedcoat coloration are homozygous dominant in one parent and homozygous recessive in the other parent. The resulting seeds are harvested in bulk and are separated on the basis of the soybean seedcoat coloration. Soybean plants resulting from the planting of the seeds capable of forming $F_1$ hybrids upon self-pollination form seeds which substantially uniformly exhibit maternally-derived light-colored seedcoats in the $F_2$ generation thereby enabling the grower to produce a substantially uniform soybean harvest. The other seeds formed in the initial planting area are capable of substantially uniformly forming restorer soybean plants in a subsequent planting.

56 Claims, 1 Drawing Sheet

4,763,441

PROCESS FOR FORMING SUBSTANTIALLY UNIFORM SEED ASSEMBLAGES CAPABLE OF GROWING $F_1$ HYBRID AND RESTORER SOYBEAN PLANTS

BACKGROUND OF THE INVENTION

Soybeans (i.e., seeds of *Glycine max*) are recognized to be an important oilseed crop in many parts of the world. For instance, approximately 65 to 75 million acres of soybeans are planted annually in the United States. Heterosis or hybrid vigor now advantageously can be used to increase the desired soybean yield in view of recent progress in this area.

Early work with respect to hybrid soybean production is disclosed in U.S. Pat. Nos. 3,903,645 and 4,077,157 to Bradner. These approaches have not become a commercial reality.

In commonly assigned U.S. Pat. Nos. 4,545,146 and 4,648,204 to Davis are disclosed novel routes to hybrid soybean production employing cytoplasmic male sterility and pollen transport by insects. These approaches are believed to provide a means for making hybrid soybeans a reality for farmers. However, when practicing such hybrid soybean production routes it previously has been considered to be important that the cytoplasmically male sterile plants and restorer male fertile plants be grown in adjacent strips in substantially uniform populations, and the resulting seeds harvested separately if one is to obtain the seeds capable of growing $F_1$ hybrid soybean plants in a substantially pure form. In many states of the United States it is essential that the soybean seeds be of at least 95 percent purity if they are to be labelled a hybrid when marketed. Such split planting and selective harvesting significantly adds to the cost of the hybrid soybean production and inherently carries with it the potential for harmful error during either or both of these operations or during subsequent seed handling. It is also important for the soybean grower to be provided with $F_1$ hybrid soybean planting seed which upon self-pollination will make possible a uniform harvest wherein substantially all of the resulting $F_2$ seeds will possess the usual light-colored seedcoat so that the harvest will qualify for the highest available soybean grade.

In U.S. Pat. No. 3,842,538 to Barabas is discussed a method involving cytoplasmic male sterility and wind pollination for forming dissimilar $F_1$ hybrid seed-grains on monocotyledons (i.e., cereals such as wheat) in which a color marker is placed in the seed pericarp of one of the parents (preferably the male), and the parent plants are planted in bulk. The seed pericarp there discussed is not maternal tissue and is non-analogous to the maternally-derived seedcoat which exists in a pod-forming legume crop such as soybeans. There is no discussion of the genetics involved in the Barabas process or how one could come into possession of the unusual crimson pericarp marker there discussed. If the crimson pericarp was dominantly transmitted (which may be likely) and present on the male parent, the process would be inoperative since all of the resulting offspring would possess a crimson pericarp and could not be separated on the basis of color. If the crimson pericarp was recessively transmitted and present on the male parent, any seeds produced by the grower upon self-pollination of the plants resulting from the growing of the $F_1$ hybrid seed would segregate as to color thereby significantly lowering the grade of the seed-grain harvest. Also, the seed-grain (e.g., wheat) formed on the male parent of Barabas would tend to be less than pure because of the unreliability of the wind pollination involved in its formation and would tend to be discarded or scraped as stated at the bottom of Col. 1.

In commonly assigned copending U.S. Ser. No. 001,227, filed Jan. 6, 1987, to Calub is disclosed a specifically defined process for producing hybrid rice using cytoplasmic male sterility, bulk planting, and seed separation on the basis of seed hull color (as described).

It is an object of the present invention to provide an improved process for simultaneously forming in the same planting area (1) seeds capable of growing $F_1$ hybrid *Glycine max* plants, and (2) seeds capable of growing restorer plants for the same.

It is an object of the present invention to provide an improved process for forming seeds capable of growing $F_1$ hybrid *Glycine max* plants wherein a substantially random population of cytoplasmically male sterile and restorer parent soybean plants is grown in a planting area and pollen transfer is accomplished with the aid of pollen-carrying bees.

It is an object of the present invention to provide an improved process for the production of substantially uniform assemblages of (1) seeds capable of growing male fertile $F_1$ hybrid *Glycine max* plants, and (2) seeds capable of growing restorer plants for use in the production of the same.

It is an object of the present invention to provide an improved hybrid soybean production process wherein the $F_1$ hybrid soybean plants resulting from the planting of the seeds capable of forming the same upon self-pollination form seeds which substantially uniformly exhibit maternally-derived light-colored seedcoats in the $F_2$ generation thereby enabling the grower to produce a substantially uniform soybean harvest.

It is another object of the present invention to provide an improved process for the formation of seeds capable of growing $F_1$ hybrid *Glycine max* plants involving cytoplasmic male sterility wherein the costly strip planting of the parent plants is avoided and the parent plants are randomly grown in the same planting area.

It is a further object of the present invention to provide an improved process for the formation of seeds capable of growing $F_1$ hybrid *Glycine max* plants wherein seeds formed on each of the parent plants simultaneously can be harvested in bulk and subsequently separated with accuracy.

It is yet another object of the present invention to provide an improved process for the formation of seeds capable of growing hybrid $F_1$ hybrid *Glycine max* plants wherein the tedious selective harvesting of seeds formed on alternating strips of plants is avoided and the plants are grown in a configuration wherein pollen transfer by pollen-carrying bees readily is accomplished.

These and other objects as well as the scope, nature, and utilization of the claimed invention will be apparent to those skilled in the art from the following detailed description and appended claims.

SUMMARY OF THE INVENTION

Figure 1:
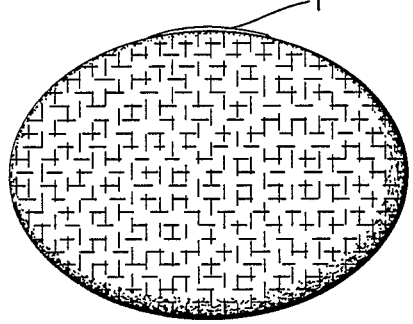
FIG. 1 illustrates a representative soybean seed suitable for use in the improved process of the present invention having a maternally-derived seedcoat which is yellow over all of its surface attributable to homozygous dominant genes for such trait.

An improved process is provided for the efficient production of substantially uniform assemblages of seeds capable of growing male fertile $F_1$ hybrid *Glycine max* plants and seeds capable of growing restorer plants for use in the production of the same comprising:

(a) growing in a planting area a substantially random population of (i) cytoplasmically male sterile soybean plants which form seeds possessing maternally-derived homozygous dominant light-colored seedcoats attributable to the presence of homozygous dominant genes, and (ii) male fertile restorer soybean plants which form seeds possessing maternally-derived seedcoats which are dark-colored over at least a portion of their surfaces attributable to the presence of homozygous recessive genes and when crossed with the cytoplasmically male sterile soybean plants enable the formation of seeds on the cytoplasmically male sterile soybean plants which are capable of growing male fertile $F_1$ hybrid soybean plants which upon self-pollination form seeds which substantially uniformly exhibit maternally-derived light-colored seedcoats, (b) forming pollen on the male fertile restorer soybean plants (ii) which is substantially non-aerodynamic and substantially incapable of being airborne, (c) crossing the cytoplasmically male sterile soybean plants (i) and the male fertile restorer plants (ii) with the aid of pollen-carrying bees wherein seeds are formed on the soybean plants (i) having maternally-derived light-colored seedcoats and seeds are formed on the soybean plants (ii) as a result of self-pollination having maternally-derived seedcoats which are dark-colored over at least a portion of their surfaces, (d) harvesting in bulk the seeds formed on the plants (i) and (ii) of the planting area, and (e) separating the seeds obtained in the harvesting step (d) on the basis of seedcoat color so as to obtain a substantially uniform assemblage of seeds derived from soybean plants (i) which possess light-colored seedcoats, and are capable of forming $F_1$ hybrid soybean plants which upon self-pollination form $F_2$ seeds which substantially uniformly exhibit maternally-derived light-colored seedcoats thereby enabling the grower to produce a substantially uniform soybean harvest with respect to seedcoat coloration, and to obtain as a result of the separation a substantially uniform assemblage of seeds derived from soybean plants (ii) which are capable of growing male fertile restorer soybean plants suitable for use in step (a) if said process is repeated.

An improved process is provided for the efficient production of substantially uniform assemblages of seeds capable of growing male fertile $F_1$ hybrid *Glycine max* plants and seeds capable of growing restorer plants for use in the production of the same comprising:

(a) growing in a planting area a substantially random population of (i) cytoplasmically male sterile soybean plants which form seeds possessing maternally-derived homozygous recessive dark-colored seedcoats attributable to the presence of homozygous recessive genes, and (ii) male fertile restorer soybean plants which form seeds possessing maternally-derived seedcoats which are light-colored over at least a portion of their surfaces attributable to the presence of homozygous dominant genes and when crossed with the cytoplasmically male sterile soybean plants enable the formation of seeds on the cytoplasmically male sterile soybean plants which are capable of growing male fertile $F_1$ hybrid soybean plants which upon self-pollination form seeds which substantially uniformly exhibit maternally-derived light-colored seedcoats, (b) forming pollen on the male fertile restorer soybean plants (ii) which is substantially non-aerodynamic and substantially incapable of being airborne, (c) crossing the cytoplasmically male sterile soybean plants (i) and the male fertile restorer plants (ii) with the aid of pollen-carrying bees wherein seeds are formed on the soybean plants (i) having maternally-derived dark-colored seedcoats and seeds are formed on the soybean plants (ii) as a result of self-pollination having maternally-derived seedcoats which are light-colored over at least a portion of their surfaces, (d) harvesting in bulk the seeds formed on the plants (i) and (ii) of the planting area, and (e) separating the seeds obtained in the harvesting step (d) on the basis of seedcoat color so as to obtain a substantially uniform assemblage of seeds derived from soybean plants (i) which possess dark-colored seedcoats, and are capable of forming $F_1$ hybrid soybean plants which upon self-pollination form $F_2$ seeds which substantially uniformly exhibit maternally-derived light-colored seedcoats thereby enabling the grower to produce a substantially uniform soybean harvest with respect to seedcoat coloration, and to obtain as a result of the separation a substantially uniform assemblage of seeds derived from soybean plants (ii) which are suitable for use in step (a) if the process is repeated.

DESCRIPTION OF PREFERRED EMBODIMENTS

The process parameters of the present invention enable one to carry out the processes of commonly assigned U.S. Pat. Nos. 4,545,146 and 4,648,204 in an improved manner. The disclosures of these patents are herein incorporated by reference.

It is essential that the female parent *Glycine max* plants be female fertile and possess cytoplasmic male sterility, and for the male parent plants to be both female and male fertile and capable of restoring fertility in the offspring. It further is essential that the parent soybean plants be provided with distinctly colored maternally-derived seedcoats wherein the genes for seedcoat coloration are homozygous dominant in one parent and homozygous recessive in the other parent. Since soybeans belong to the Leguminosae family and bear pods, the seedcoats are formed exclusively of maternal tissue and are not influenced by the male gametes which fertilized the plant embryo to cause seed formation. In a preferred embodiment the seedcoat coloration is controlled by single pairs of genes present in each of the mother plants. Also, in a preferred embodiment such genes are homozygous recessive for a distinctive dark-colored seedcoat in the male parent and homozygous dominant for a distinctive light-colored seedcoat in the female parent. However, such seedcoat colorations can be reversed in the parents and still obtain satisfactory results. It is to be understood that the soybean seedcoat colorations discussed herein are those colorations which are exhibited when the soybeans are mature at the time of harvest.

Suitable light-colored soybean seedcoats commonly are yellow in coloration over substantially all of their surfaces. A soybean having a yellow seedcoat is illustrated in FIG. 1 wherein the hilum 1 is shown. The term yellow as used herein includes color variations, such as off-white, yellow-white, yellow-orange, etc. Such light-colored seedcoats are dominantly transmitted and are controlled by genes present in the mother plant. Suitable dominant genes which are known to impart a yellow seedcoat include I and $i^i$. The coloration of the hila where the soybeans attach to the pod may vary. Soybeans possessing yellow seedcoats include the most commonly available commercial varieties as well as the cytoplasmically male sterile forms thereof. For instance, commercially available soybean varieties which exhibit yellow seedcoats include: 4404, 4503, 9091, 9181, 9201, 9202, 120004, A 949, A 1179, A 1564, A 3127, A 3659, A 3866, A 4268, A 4298, A 4997, A 5474, AP 120, AP 240, AP 3132, B 117, B 152, B 236, CM 048, CM 243, CM 269, CM 274, CM 340, CM 368, CM 379, CX 096, CX 117, CX 134, CX 264, CX 285, DPL 105 CMS, DPL 403, DSR 212, FFR 226, FFR 557, FFR 668, G 3180, G 3440, G 3443, GT 1170, GT 1200, GT 1250, GT 1270, GT 1310, GT 1330, GT 1340, GT 1380, HP 4800, J-103, J-431, L 4207, L 4504, LH 106, NK 1346, NK 1474, NK 1492, NK 54055, OX 611, OX 619, RA 203, RA 405, RA 451, RA 604, RA 680, 29-20, S 23-12, S 30-31, S 33-45, S 72-60, SO 657, SRF 101, SRF 205, SRF 307, SRF 307B, SRF 400, SRF 425, SRF 450, SRF 150P, SRF 270P, SRF 301P, SSRF 450P, VR 4004, VR 8001, VR 8027, VR 8041407, VR 8041494, VR 9120942, VR 9120943, VR 9120990, Amsoy 71, Bedford, Callahan 1450, Callahan 1460, Callahan 2380, Coker 156, Coker 237, Corsoy, Forrest, Germplasm M70-187, Gold Tax 1440, Max, Migro Ho 4800, Mitchell 410, Mitchell 450, Pioneer, 4880, Pride B 202, Terra Vig 606, Terra Vig 708, Tracy M, Shiloh, Stein 2210, Voris 227, Voris 465, Voris 477, Voris 495, Wilstar 430, Wilstar 550, Yield King 613, etc.

Figure 2:
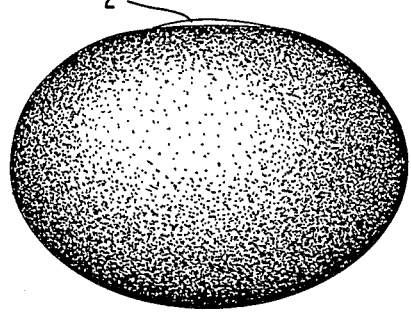
FIG. 2 illustrates a representative soybean seed suitable for use in the improved process of the present invention having a maternally-derived seedcoat which is black over all of its surface attributable to homozygous recessive genes for such trait.
Figure 3:
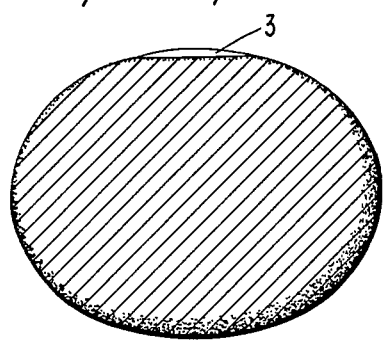
FIG. 3 illustrates a representative soybean seed suitable for use in the improved process of the present invention having a maternally-derived seedcoat which is brown over all of its surface attributable to homozygous recessive genes for such trait.
Figure 4:
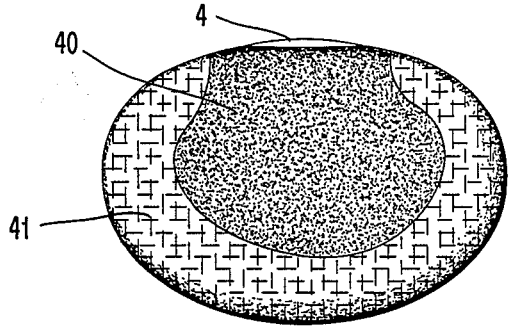
FIG. 4 illustrates a representative soybean seed suitable for use in the improved process of the present invention having a maternally-derived seedcoat which has a black saddle area over a portion of its surface.
Figure 5:
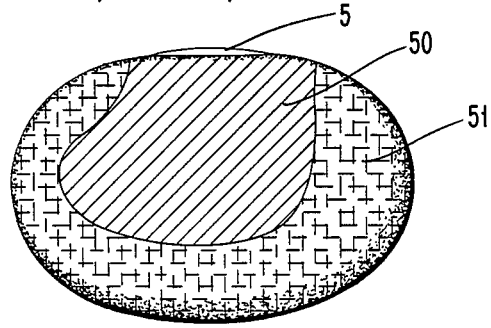
FIG. 5 illustrates a representative soybean seed suitable for use in the improved process of the present invention having a maternally-derived seedcoat which has a brown saddle area over a portion of its surface.

The dark-colored soybean seedcoats commonly are black or brown over at least a portion of their surfaces. The term black as used herein includes variations thereof such as gray and imperfect black (i.e., black over brown). The term brown as used herein includes variations thereof such as buff and red-brown. Such dark-colored seedcoats are recessively transmitted and are controlled by genes present in the mother plant (i.e., commonly a single pair of genes). A soybean having a black seedcoat is illustrated in FIG. 2 wherein the hilum 2 is shown, and a soybean having a brown seedcoat is illustrated in FIG. 3 wherein the hilum 3 is shown. Such seedcoat colorations frequently are controlled by i genes. In those instances in which the dark coloration extends over only a portion of the seedcoat, such dark coloration commonly is present as irregularly shaped saddle areas adjacent the hila with the remainder of the seedcoats being light-colored. In FIG. 4 is illustrated a soybean having a hilum 4, a black saddle 40, and a balance 41 of the seedcoat which is yellow. In FIG. 5 is illustrated a soybean having a hilum 5, a brown saddle 50, and a balance 51 of the seedcoat which is yellow. Such dark saddle seedcoat colorations frequently are controlled by $i^k$ genes.

Soybeans suitable for use in the process of the present invention which possess dark coloration on their seedcoats can be obtained from conventional sources. The soybeans need only be visually observed to see if they possess this seedcoat trait. In a preferred embodiment such soybeans having a dark coloration over at least a portion of their surfaces are derived from a spontaneous mutation which has been found to occur in a substantially pure soybean line which normally produces soybeans having light-colored seedcoats. For instance, I genes can mutate to i or $i^k$, and $i^i$ genes can mutate to i or $i^k$ genes. Such mutation can be found with relative ease. One need only to inspect bags of commercially available soybean planting seeds of varieties which normally possess yellow seedcoats. Within most 60 pound bags one can visually identify a few soybeans (e.g., 2 to 20 seeds) having dark-colored seedcoats which are the result of a spontaneous mutation. Alternatively, the desired soybean seedcoat coloration can be introduced into a given variety by backcrossing. It has been found that the resulting dark seedcoat coloration is genetically linked to the hilum coloration.

For instance, commercially available soybean varieties such as 5482, 6727, 6738, 6782, 9331, 9361, 9391, 9401, 9441, 9442, 9471, 9561, 9571, 9581, 9641, 9751, 12277, A 237, A 1895, A 2943, A 3127, A 3420, A 3659, A 3860, A 3966, A 4271, A 5474, A 5939, A 5980, A 6242, A 6520, A 6785, A 7372, A 7986, AP 330, AP 2021, Ap 3773, Ap 3977, Ap 4321, CM 176, CM 242, CM 473, CX 324, CX 326, CX 366, DP 726, DPF 345, DPL 439, DPL 497, DPL 506, DSR 066, DSR 205, DSR 255, DSR 287, DSR 317, FFR 241, FFR 332, FFR 339, FFR 441, FFR 451, FFR 557, FFR 562, FFR 666, FR 448, G 3232, G 3236, G 3340, GL 4200, HP 963, HP 3440, J 112, J 231, J 271, J 331, J 471, J 541, L 2456, L 4101, OX 299, OX 693, RA 31, RA 36, RA 63, RA 66, RA 401, RA 403, RA 404, RA 451, RA 480, RA 501, RA 501A, RA 502, RA 580, RA 581, RA 603, RA 604, RA 680, RA 680, RA 701, RA 702, RA 800, RA 801, S 42-40, S 53-34, SB 4150, SB 4500, SRF 300, SRF 350P, SX 760(I)22, SX 760(I)36, SX 760(i)64A, 21J1942, Bedford, Bragg, Calland, Coker 237, Coker 627, Coker 686, Deltapine 105, Deltapine 246, Deltapine 345, Deltapine 506, Forrest, Hartz 5252, Hartz 5370, Hartz 7126, Hartz 9190, Hartz 6383R, Pride B 242, Shiloh, Tracey M, Voris 147, Voris 257, Williams, Wilstar 790, Woodworth, etc., are known to normally exhibit black hila and yellow seedcoats attributable to $i^i$ genes. These have been found to spontaneously undergo either of a pair of mutations which produce (1) all black seedcoats such as that illustrated in FIG. 2 which are attributable to i genes, or (2) black saddles upon the otherwise light-colored seedcoats such as that illustrated in FIG. 4 which are attributable to $i^k$ genes.

Also, commercially available soybean varieties such as 606, 9251, 9271, 9292, A 1937, A 2522, A 2575, A 2680, A 5312, A 5618, Ap 420, Ap 1776, Ap 3023, CM 145, CM 246, CM 266, CM 370, CM 442, CX 174, CX 187, CX 226, CX 254, CX 453, CX 482, DPL 675, DSR 128, DSR 135, DSR 151, DSR 297, DSR 312, EXP 338, EXP 432, FFR 225, FFR 561, FFR 777, G 3197, J-82, J-201, L 4204, L 4303, M 760815, OX 696, OX 298, RA 280, RA 303, RA 380, RA 402, RA 405, RA 452, RA 481, RA 526, RA 606, RA 700, S 14-60, S 23-03, S 39-93, S 44-77, S 45-01, S 69-96, SRF 220, SSRF IOOP, Coker 156, Deltapine 497, Duocrop, Hartz 5171, Hodgson 78, McNair, 500, Mitchell, Mitchell 410, Mitchell 450, Voris 251, Yield King 613, etc., are known to normally exhibit brown hila and yellow seedcoats attributable to I genes. These have been found to spontaneously undergo either of a pair of mutations which produce (1) all brown seedcoats such as that illustrated in FIG. 3 which are attributable to i genes, or (2) brown saddles upon the otherwise light-colored seedcoats such as that illustrated in FIG. 5 which are attributable to $i^k$ genes.

If it is desired to place the dark-colored seedcoat in the cytoplasmically male sterile parent, this can be accomplished by a conversion process in which the dark-colored seedcoat characteristic is first introduced into a maintainer line for the cytoplasmically male sterile parent followed by a series of self-pollinations and selections. The resulting maintainer having the desired dark-colored seedcoat next is crossed a plurality of times with the cytoplasmically male sterile plants.

In accordance with preferred embodiments of the present invention, the cytoplasmically male sterile plants possessing the requisite seedcoat coloration are otherwise as described in U.S. Pat. Nos. 4,545,146 and 4,648,204. As there discussed, three factors found to exist in available sources of *Glycine max* plants, when properly combined in a single plant provide an effective female parent starting plant to accomplish the hybrid soybean production. Such factors (as described hereafter) have heretofore existed separately while dispersed in soybean plants from widely differing sources. The female fertile male sterile soybean plants possess (1) a Cms cytoplasm, (2) a distinct pair of recessive $r_1r_1$ genes in the cell nucleus, and (3) a distinct pair of recessive $r_2r_2$ genes in the cell nucleus, which in combination render the plant incapable of producing viable pollen while otherwise carrying out the usual plant functions required to produce soybeans if viable pollen is provided from another soybean plant.

The Cms cytoplasm of the preferred female fertile male sterile soybean plants can be derived through the female parent from an appropriate cytoplasmic source. For instance, it has been found that the Cms cytoplasm required in the female fertile fully male sterile soybean plants can be conveniently derived from the Mandarin cytoplasmic source through the female parent. Many Northern United States varieties are derived from this cytoplasmic source. Plants of this origin have been found inherently to possess a cytoplasm of the type required to practice the present invention. Since this required factor is not contributed by nuclear genes and is not transmitted through the pollen, it can be considered cytoplasmic, non-Mendelian, extrachromosomal, uniparental, and maternal. Representative commercially available soybean plants which are derived maternally from a Mandarin cytoplasmic source are Adelphia, Chippewa, Chippewa 64, Clark, Classic I, Classic II, Columbus, Cutler, Disoy, Elf, Ford, Grant, Harosoy, Harosoy 63, Hobbitt, Kent, Lincoln, Lindarin, Lindarin 63, Magna, Prize, Provar, Rampage, RA 203, RA 402, RA 481, RAX 56, RAX 57, RAX 61, RAX 62, RAX 66, SB 27, Shelby, Traverse, Wayne, Wirth, Williams, etc. A particularly good source for the required Cms cytoplasm has been found to be the Elf variety which was introduced during 1977 by AR-SEA-USDA, the Ohio Agric. Res. and Dev. Center, and the U. of Illinois Agric. Res. Station. In 1981 this variety was registered by the Crop Sci. Soc. of Am. as Reg. No. 150.

It should be emphasized that when plants of the above-identified varieties are inspected for the possible absence of viable pollen production, that male sterile plants wherein the sterility is attributable to the cytoplasm are not observed. It has been found that such sterility is not expressed even though the required Cms cytoplasm is present because it not in combination with the required recessive genes discussed hereafter. Instead such varieties can be shown to possess at least one pair of dominant $R_1R_1$ or $R_2R_2$ genes (usually both pairs) which always leads to the expression of the usual viable pollen production even in the presence of the Cms cytoplasm.

The pair of recessive genes $r_1r_1$ for male sterility present in the preferred female fertile fully male sterile plants employed in the process of the present invention can be derived through its male parent from a first gene source which possesses such genes. Unlike the male sterile plants, the first gene source may possess an N cytoplasm which can be termed a "normal" or "neutral" cytoplasm. When such cytoplasm is present, cytoplasmically controlled male sterility is not exhibited regardless of the nuclear genes which are present.

It has been found that the requisite pair of $r_1r_1$ recessive genes in the cell nucleus of the female fertile fully male sterile soybean plants conveniently can be derived through the male parent from a Dunfield germplasm base. Many Southern soybean varieties are derived from this germplasm base. Plants of this origin have been found inherently to possess the required pair of recessive genes which has been designated $r_1r_1$. Representative commercially available soybean plants from which the $r_1r_1$ recessive genes may be derived are Bedford, Bethel, Centennial, Dare, Dyer, Forrest, Hill, Kirby, RA(d)41, RA 581, RA 603, RA 605, RA 606, RA 680, Tracy, Wabash, York, etc. A particulary good source for the $r_1r_1$ recessive genes has been found to be the Bedford variety which was introduced during 1978 by FR-SEA-USDA, and the Tennessee and Mississippi Agric. Expt. Stations. This variety was registered by the Crop Sci. Soc. of Am. as Reg. No. 118.

It further should be emphasized that when plants of the above-identified varieties having $r_1r_1$ genes are inspected for the possible absence of viable pollen production, that male sterile plants wherein the sterility is attributable to the cytoplasm are not observed. It has been found that such sterility will not be expressed unless the Cms cytoplasm is present along with recessive genes $r_2r_2$. Instead, such varieties can be shown to possess dominant $R_2R_2$ genes which restore male fertility.

The pair of recessive genes $r_2r_2$ for male sterility present in the preferred female fertile fully male sterile plants can be derived through its male parent from a second gene source which possesses such genes. Such $r_2r_2$ genes are present as a distinct gene pair apart from the $r_1r_1$ genes in the female fertile fully male sterile plants (i.e., they are present at different loci). Unlike the male sterile plants, the second gene source may possess an N cytoplasm which can be termed a "normal" or "neutral" cytoplasm. As previously indicated, when such cytoplasm is present, cytoplasmically controlled male sterility is not exhibited regardless of the nuclear genes which are present.

It has been found that the requisite pair of $r_2r_2$ recessive genes in the cell nucleus of the preferred female fertile fully male sterile soybean plants conveniently can be derived through the male parent from a Tokyo germplasm base. Many Southern soybean varieties are derived from this germplasm base. Plants of this origin have been found inherently to possess the required pair of recessive genes which has been designated $r_2r_2$. Representative commercially available soybean plants from which the $r_2r_2$ recessive genes may be derived are Bragg, Braxton, Cobb, Govan, Hampton, Hampton 266, Hardee, Hutton, Jackson, Kirby, Majos, Ogden, RA 604, RA 701, RA 800, Volstate, Wright, etc. A particularly good source for the $r_2r_2$ recessive genes has been found in the Braxton variety which was introduced during 1979 by the USDA and various state Agric. Expt. Stations.

It additionally should be emphasized that when plants of the above-identified varieties having $r_2r_2$ genes are inspected for the possible absence of viable pollen production, that male sterile plants where the sterility is attributable to the cytoplasm are not observed. It has been found that such sterility will not be expressed unless the Cms cytoplasm is present along with recessive genes $r_1r_1$. Instead such varieties can be shown to possess dominant $R_1R_1$ genes which restore male fertility.

The preferred female fertile fully male sterile plants can be maintained or perpetuated in spite of the male sterility by crossing with pollen from a soybean plant which possesses an N cytoplasm and the two distinct pair of recessive genes $r_1r_1$ and $r_2R_2$. Such preferred maintainer plants are formed through the combination of the required factors and are not found in nature. The progeny of this cross will again be female fertile and fully male sterile. Also, should the preferred female fertile fully male sterile plants be crossed with pollen from a male fertility restorer (i.e., having dominant $R_1R_1$ genes and/or dominant $R_2R_2$ genes), then the progeny will be fully fertile $F_1$ hybrid soybean plants. As previously discussed, suitable male fertility restorer plants possessing the requisite seedcoat coloration are available without modification. For instance, varieties heretofore named can perform this function provided plants with the proper seedcoat coloration are selected. The only requirement in addition to seedcoat coloration is that plants which supply the pollen possess at least one pair of the required dominant fertility restoring genes.

The development of preferred female fertile fully male sterile soybean plants for use in the present invention, as well as preferred maintainer plants for the same, can be exemplified through a plant breeding program employing plants of the Elf, Bedford, and Braxton varieties. It should be understood, however, that the preferred embodiment of the present process can be equally well practiced through the utilization of soybean plants of other varieties provided the essential criteria set forth herein nevertheless are met. Initially plants of the Bedford variety (i.e., having an $r_1r_1$ gene source) are crossed by hand with pollen from plants of the Braxton variety (i.e., having an $r_2r_2$ gene source). The progeny of this cross are fully female fertile and male fertile and serve as a pollen source for plants of the Elf variety (i.e., having a Cms cytoplasmic source). Such crossing to the Elf variety is again carried out by hand under controlled conditions in the absence of Elf self-pollination. When the $F_1$ seed which has formed on the Elf female parent is grown, it will be noted that all of the resulting plants are fully female fertile and male fertile. Each of these $F_1$ plants is next self-pollinated through succeeding generations to form $F_2$, $F_3$, and $F_4$ controlled populations which are inspected for the absence of viable pollen. It is observed that some plants are female fertile male fertile, and some plants are female fertile male sterile (i.e., produce no viable pollen).

Once the preferred male sterile plants are on hand, suitable maintainer plants (i.e., those having an N cytoplasm in combination with $r_1r_1$ and $r_2r_2$ genes) can be developed by standard plant breeding techniques involving intercrossing and introgression. For instance, the required $r_1r_1$ and $r_2r_2$ genes can be provided in existing soybean varieties of agronomic importance having an N cytoplasm by intercrossing and possible backcrossing by hand with the pollen derived from plants obtained from the $F_2$, $F_3$ and $F_4$ controlled populations obtained during or subsequent to the development of the male sterile plants. The $F_1$ plants from this cross are grown and are self-pollinated to form $F_2$ plants. Test crosses of the fully male sterile plants previously developed with pollen derived form the $F_2$ plants are made and those plants are identified and preserved which are capable of yielding fully male sterile $F_1$ progeny. Such plants possess the full complement of recessive $r_1r_1$ and $r_2r_2$ genes. Once identified such preferred homozygous maintainer plants can be perpetuated by self-pollination.

Since the photosensitivity of soybean plants tends to vary among soybean varieties, it is important for best results that the parent soybean plants (i.e., the cytoplasmically male sterile soybean plants and the male fertile restorer soybean plants) each possess a day length sensitivity (i.e., a photoperiod response) which generally corresponds to that of the location (i.e., the latitude or distance from the equator) where the soybean plants are grown when carrying out the process of the present invention as well as to the area where the seed product is ultimately to be grown. For instance, the parent plants and the ultimate seed product preferably should possess a photosensitivity within plus or minus one maturity group unit of the locations where grown. Additionally, for optimum results the locations where grown should correspond exactly to the maturity groups of the plants involved. See, Chapter 6 by Edgar E. Hartwig of "Soybeans: Improvement, Production, and Uses", American Society of Agronomy, Inc., Pages 189 to 190 (1973) which is herein incorporated by reference, for a discussion of soybean maturity group units and their significance. For instance, if a soybean variety which grows well at a southern latitude is grown at a northern latitude, the longer days may cause the soybean plants to grow excessively tall and to tend to lodge. Alternatively, if a soybean variety which grows well at a northern latitude is grown at a southern latitude, the shorter days may cause limited plant growth (i.e., height) and result in poor yields.

In a preferred embodiment male and female parent soybean plants are selected which possess substantially the same height at the time pollination is carried out with the aid of pollen-carrying bees. The flowers of each parent plant should be as attractive to bees as possible. Also, it is preferred that the male and female parents used in the process of the present invention possess substantially the same flower color. Purple colored blossoms particulary are preferred because of their attractiveness to bees. Also, in a preferred embodiment it is preferred that the flowering period for the male fertile restorer soybean plants commences before the flowering period for the cytoplasmically male sterile soybean plants and ends thereafter. This helps to assure that pollen will be available when it is needed to pollinate the female parent plants. Also, the bees can more readily accomplish the desired pollination if all blossoms are at approximately the same height and the flower coloration is substantially the same. Accordingly, a flower color preference does not influence the routes travelled by the pollen-carrying bees.

In accordance with a preferred embodiment the process of the present invention the parent soybean plants are grown at a location which normally experiences limited natural rainfall during the summer months when soybean flowers normally are formed and cross-pollination is carried out with the aid of pollen-carrying bees as described in U.S. Pat. No. 4,648,204. It will be understood, however, that the process of the present invention also can be carried out at any location in the northern or southern hemispheres where the soil will support the growth of soybean plants in the absence of irrigation.

It is preferred that the area selected be one in which there is a relatively low pesticide usage, honeybees customarily are kept and are available, and a wild bee population is available.

A substantially random population of the two parent plants is grown in the planting area when carrying out the process of the present invention. Such random planting of both parents within the same rows has been found to greatly aid the desired visitation by pollen-carrying bees since bees have a greater propensity to travel down rows of soybean plants rather than across rows of soybean plants. The relative proportions of the parent plants can be varied so long as adequate pollen is provided by the male parent plants to substantially completely pollinate the female parent plants. In a preferred embodiment approximately 75 to 85 percent of cytoplasmically male sterile soybean plants are present with approximately 15 to 25 percent of male fertile restorer soybean plants. In a particularly preferred embodiment approximately 80 percent of cytoplasmically male sterile soybean plants are present with approximately 20 percent of male fertile restorer plants. Conventional planting times and techniques can be used when planting a random blend of seeds capable of forming the two parent plants.

In accordance with a preferred embodiment of the present invention, water is applied via irrigation to the seeds which produce the cytoplasmically male sterile and male fertile restorer soybean plants following planting in an area which normally experiences limited natural rainfall so as to accomplish seed germination and normal plant growth up to at least the time of the onset of flower formation on each of the two plant types. The quantity of water applied will be influenced by the frequency and extent of natural rainfall (if any). The manner in which the irrigation water is applied may be varied and commonly will correspond to the irrigation technique that may be most conveniently implemented at the particular location which normally experiences limited natural rainfall. As will be apparent to those skilled in agronomic technology, the particular irrigation technique selected will also be influenced by the soil type encountered and its inherent water-holding capabilities. Light soils will inherently require lesser irrigation amounts and more frequent water applications. Representative irrigation techniques that may be selected include (1) sprinkler systems whereby water is sprayed and impacts upon the planting area from overhead through the air, (2) flooding systems whereby water confined by a levy or other means is caused to flow upon the surface of the soil and to substantially completely engulf the planting area, (3) furrow systems whereby a furrow is mechanically cut in the soil adjacent to the locations where the soybean plants are grown and is filled with water, etc. Sprinkler systems commonly have the advantage of using less water. In northeastern Arkansas commonly a flooding system will be employed. In western Texas commonly a furrow system or a sprinkler system will be employed. Also commonly, the water is applied via irrigation for a period of approximately 0.1 to 15 days (or more) prior to the withholding of irrigation water (as described hereafter). The duration of the time in which water is applied by irrigation will primarily be influenced by the natural rainfall (if any), the other weather conditions (e.g., heat and humidity) encountered, and the ability of the soil to hold water once irrigation is commenced. In any event, water may be applied as required via irrigation in sufficient quantities and at sufficient intervals to insure normal soybean plant growth up to at least the time when flowers are present on each of the parent plant types.

The application of water via irrigation promotes the normal vegetative growth of the soybean plants and flower formation. The nectar exuded by the resulting soybean flowers, when irrigation and/or natural rainfall is taking place, tends to be more dilute and is considerably less attractive to bees than that formed when irrigation water is withheld from the planting area.

It should be recognized that male fertile restorer soybean plants inherently form pollen which is substantially non-aerodynamic and substantially incapable of being airborne. Accordingly, wind cannot be relied upon to bring about the desired cross-pollination. The process of the present invention utilizes pollen-carrying bees to bring about the required cross-pollination of the parent soybean plants. At most growing areas honeybees are particularly effective in bringing about the desired cross-pollination. However, bees other than honeybees can alternatively be employed so long as they will reliably visit the soybean flowers at the appropriate time. For instance, leaf-cutter bees (i.e., *Megachile rotundata*) can be used. Also, naturally occurring bees other than honeybees and leaf-cutter bees (i.e., wild bees) advantageously may supplement the level of cross-pollination. Bees appear to visit soybean plants primarily in search of nectar and to a lesser extent for pollen that serves as a protein source for the bees. As bees collect nectar, they concomitantly serve to pick up and carry pollen from one soybean plant to another.

In a preferred embodiment of the process of the present invention, one or more honeybee hives are situated in pollinating proximity to the location where the parent soybean plants are being grown in order to insure the ample presence of sufficient pollen vectors. For instance, in a particularly preferred embodiment, honeybee hives are provided in pollinating proximity to the location where the parent soybean plants are being grown at a rate of at least 2 hives per acre (e.g., 2 to 3 hives per acre) of the parent soybean plants. If irrigation is accomplished by flooding, the hives may be situated on a small terrace above the water level. It further is preferred that a route be provided in the planting area to provide ready ingress and egress for the beekeepers having the responsibility of servicing the beehives. For best results, it is recommended that the honeybee hives be positioned so that the honeybees are not required to travel more than approximately one-quarter of a mile to visit the parent soybean plants. This tends to improve the foraging efficiency.

Since pollen serves as a protein source required by bees and soybean plants tend not to produce pollen in profuse quantities, it is preferred that a supplemental protein source for the pollen-carrying bees be provided in addition to the pollen formed on the male parent soybean plants in order to more fully support the pollen requirements of the pollen-carrying bees. Such supplemental protein source for the enrichment of the bee diet may take various forms. For instance, plants known to form pollen in relatively copious quantities (e.g., sorghum, sudan, pearl millet, etc.) can be grown nearby. Alternatively, a concentrated pollen source, such as pollen cakes available to beekeepers, can be placed in the vicinity of or within the honeybee hives.

Insecticides must be used with care in the planting area since adult bees may be killed and sometimes bees will refuse to visit fields which have been sprayed with insecticides. Accordingly, if insecticides are used they should possess a low killing potential for bees, and preferably be applied during the night or some other time when any beehives in the area are closed.

When practicing this process embodiment a high level of cross-pollination among the parent soybean plants is made possible. At an appropriate time when flowers are present on the parent soybean plants, irrigation water is withheld for a period of time during which no appreciable natural rainfall occurs in order to induce enhanced nectar within the flowers, which serves to render the flowers more attractive to bees. When irrigation water is withheld, the nectar within the soybean flowers increases substantially and the sugar component of the nectar becomes more concentrated and more aromatic. Such enhanced nectar is readily perceived by the bees that forage in the area and the bees are strongly attracted to the soybean plants. Such increased bee visitation results in higher levels of the desired cross-pollination and seed set.

It is important that the period of time during which irrigation water is withheld not exceed that which can be well tolerated by the parent plants involved (i.e., not significantly impair the plant metabolism in a way which would interfere with the desired seed set and seed formation). The duration of the period in which irrigation water is withheld at a time when no appreciable natural rainfall occurs will be influenced by the environmental conditions (e.g., temperature, humidity, wind velocity, etc.) and the water-holding ability of the soil. In a preferred embodiment, the irrigation water is withheld for a period of at least 8 days (e.g., 10 to 15 days).

At the conclusion of the period during which irrigation water is withheld, the parent soybean plants may again be watered via irrigation to promote normal plant growth in order to insure the formation of the desired seeds that subsequently are harvested at the appropriate time in their maturity cycle. However, the process steps optionally may be repeated at least one time (e.g., 1 or 2 more times) during which irrigation water is applied, irrigation water is withheld, and additional cross-pollination by pollen-carrying bees is accomplished. Such repetition of the process steps may be carried out to particular advantage when the parent soybean plants are selected that inherently flower over an extended period of time (e.g., when both of the soybean parents have indeterminate flowering characteristics). For instance, when both soybean plant parents have indeterminate flowering characteristics, irrigation water commonly is withheld for a total of 2 or 3 times (or more) during the flowering period. However, when both soybean plant parents have determinate flowering characteristics, irrigation water commonly is withheld for a total of only 1 or 2 times during the flowering period.

Following cross-pollination the seeds formed on the cytoplasmically male sterile soybean plants have a different seedcoat coloration than the seeds formed on the male fertile restorer soybean plants. Such seedcoat colorations are maternally-derived in soybeans. In preferred embodiments the soybean seeds formed on the cytoplasmically male sterile soybean plants possess light-colored seedcoats and the seeds formed on the male fertile restorer soybean plants possess dark-colored seedcoats. The resulting seeds formed in the planting area are harvested in bulk using any appropriate harvest means. For instance, a standard combine can be used to advantage to bring about the harvest.

The soybean seeds resulting from the harvest next are separated on the basis of seedcoat color so as to form two substantially uniform seed assemblages. One seed assemblage is capable of growing male fertile $F_1$ hybrid *Glycine max* plants, and the other is capable of growing male fertile restorer plants for use in the production of the $F_1$ hybrid soybean plants in another planting. Such separation preferably is mechanized. For example, photoelectric seed-sorting equipment can be utilized with the soybeans having dark-colored maternally-derived seedcoats being removed from the soybeans having light-colored maternally-derived seedcoats. Suitable photoelectric seed-sorting equipment is manufactured and offered for sale by ESM International, Inc., 10621 Harwin Dr., Suite 300, Houston, Tex. 77036, USA. For instance, Model Nos. GB104C and 2000C may be utilized to advantage. Navy bean sorters manufactured by Saketa of Japan having 3, 10 or 40 channels, also may be used to accomplish the separation of the soybeans on the basis of seedcoat color. Such machines may be obtained through the Houston, Tex. USA office of Saketa or through C. K. Brown Associates, P.O. Box Q, Twin Falls, Id. 83303 USA. The sort rate is adjusted in accordance with the manufacturer's instructions to achieve the requisite separation. Also, it is possible to send the seeds through the seed-sorting equipment more than one time to achieve the final separation. In a preferred embodiment the seeds derived from the cytoplasmically male sterile soybean plants which are capable of forming $F_1$ hybrid soybean plants are at least 95 percent pure, and at least 99 percent pure in a particularly preferred embodiment.

The overall process of the present invention significantly adds to the efficiency of the prior art processes for the production of seeds capable of growing $F_1$ hybrid soybean plants.

Although the invention has been described with preferred embodiments, it is to be understood that variations and modifications may be resorted to as will be apparent to those skilled in the art. Such variations and modifications are to be considered within the purview and scope of the claims appended hereto.

I claim:

1. An improved process for the efficient production of substantially uniform assemblages of seeds capable of growing male fertile $F_1$ hybrid *Glycine max* plants and seeds capable of growing restorer plants for use in the production of the same comprising:
   (a) growing in a planting area a substantially random population of (i) cytoplasmically male sterile soybean plants which form seeds possessing maternally-derived homozygous dominant light-colored seedcoats attributable to the presence of homozygous dominant genes, and (ii) male fertile restorer soybean plants which form seeds possessing maternally-derived seedcoats which are dark-colored over at least a portion of their surfaces attributable to the presence of homozygous recessive genes and when crossed with said cytoplasmically male sterile soybean plants enable the formation of seeds on said cytoplasmically male sterile soybean plants which are capable of growing male fertile $F_1$ hybrid soybean plants which upon self-pollination form seeds which substantially uniformly exhibit maternally-derived light-colored seedcoats,
   (b) forming pollen on said male fertile restorer soybean plants (ii) which is substantially non-aerodynamic and substantially incapable of being airborne,
   (c) crossing said cytoplasmically male sterile soybean plants (i) and said male fertile restorer plants (ii) with the aid of pollen-carrying bees wherein seeds are formed on said soybean plants (i) having maternally-derived light-colored seedcoats and seeds are formed on said soybean plants (ii) as a result of self-pollination having maternally-derived seedcoats which are dark-colored over at least a portion of their surfaces,
   (d) harvesting in bulk the seeds formed on said plants (i) and (ii) of said planting area, and
   (e) separating the seeds obtained in said harvesting step (d) on the basis of seedcoat color so as to obtain a substantially uniform assemblage of seeds derived from soybean plants (i) which possess light-colored seedcoats, and are capable of forming $F_1$ hybrid soybean plants which upon self-pollination form $F_2$ seeds which substantially uniformly exhibit maternally-derived light-colored seedcoats thereby enabling the grower to produce a substantially uniform soybean harvest with respect to seedcoat coloration, and to obtain as a result of said separation a substantially uniform assemblage of seeds derived from soybean plants (ii) which are capable of growing male fertile restorer soybean plants suitable for use in step (a) if said process is repeated.

2. An improved process for the efficient production of seeds capable of growing male fertile $F_1$ hybrid *Glycine max* plants according to claim 1 wherein the flowering period at said planting area for said male fertile restorer soybean plants (ii) commences before the flowering period for said cytoplasmically male sterile soybean plants (i) and ends after the flowering period for said cytoplasmically male sterile soybean plants (ii).

3. An improved process for the efficient production of seeds capable of growing male fertile $F_1$ hybrid *Glycine max* plants according to claim 1 wherein said soybean plants (i) and (ii) are substantially the same height at the time of said cross-pollination of step (c).

4. An improved process for the efficient production of seeds capable of growing male fertile $F_1$ hybrid *Glycine max* plants according to claim 1 wherein said soybean plants (i) and (ii) of step (a) each possess substantially the same flower coloration.

5. An improved process for the efficient production of seeds capable of growing male fertile $F_1$ hybrid *Glycine max* plants according to claim 1 wherein said soybean plants (i) an (ii) of step (a) each possess purple flowers.

6. An improved process for the efficient production of seeds capable of growing male fertile $F_1$ *Glycine max* plants according to claim 1 wherein said male fertile restorer soybean plants (ii) of step (a) are derived from a mutation which occurred in a substantially pure soybean line which normally produces seeds having light-colored seedcoats wherein the seedcoats of the mutant are dark-colored over at least a portion of their surfaces.

7. An improved process for the efficient production of seeds capable of growing male fertile $F_1$ hybrid *Glycine max* plants according to claim 1 wherein in step (a) approximately 75 to 85 percent of the plants present in said substantially random population are cytoplasmically male sterile soybean plants (i) and approximately 15 to 25 percent of the plants are male fertile restorer soybean plants (ii).

8. An improved process for the efficient production of seeds capable of growing male fertile $F_1$ hybrid *Glycine max* plants according to claim 1 wherein said maternally-derived seedcoats of said cytoplasmically male sterile soybean plants (i) of step (a) are yellow in coloration over substantially all of their surfaces.

9. An improved process for the efficient production of seeds capable of growing male fertile $F_1$ hybrid *Glycine max* plants according to claim 1 wherein said maternally-derived seedcoats of said male fertile restorer soybean plants (ii) of step (a) are black in coloration over substantially all of their surfaces.

10. An improved process for the efficient production of seeds capable of growing male fertile $F_1$ hybrid *Glycine max* plants according to claim 1 wherein said maternally-derived seedcoats of said male fertile restorer soybean plants (ii) of step (a) are brown in coloration over substantially all of their surfaces.

11. An improved process for the efficient production of seeds capable of growing male fertile $F_1$ hybrid *Glycine max* plants according to claim 1 wherein said maternally-derived seedcoats of said male fertile restorer soybean plants (ii) of step (a) possess dark-colored saddle areas adjacent the hila which extend over a portion of their surfaces.

12. An improved process for the efficient production of seeds capable of growing male fertile $F_1$ hybrid *Glycine max* plants according to claim 11 wherein said dark-colored saddle areas are black in coloration.

13. An improved process for the efficient production of seeds capable of growing male fertile $F_1$ hybrid *Glycine max* plants according to claim 11 wherein said dark-colored saddle areas are brown in coloration.

14. An improved process for the efficient production of seeds capable of growing male fertile $F_1$ hybrid *Glycine max* plants according to claim 1 wherein in step (c) said pollen-carrying bees are primarily honeybees.

15. An improved process for the efficient production of seeds capable of growing male fertile $F_1$ hybrid *Glycine max* plants according to claim 1 wherein honeybee hives are provided in pollinating proximity to said planting area of step (a) at a rate of at least 2 hives per acre of said substantially random population of soybean plants (i) and (ii).

16. An improved process for the efficient production of seeds capable of growing male fertile $F_1$ hybrid *Glycine max* plants according to claim 1 wherein a supplemental pollen source for said pollen-carrying bees is provided in addition to the pollen formed on said male fertile restorer soybean plants (ii) in order to provide ample pollen to support said pollen-carrying bees.

17. An improved process for the efficient production of seeds capable of growing male fertile $F_1$ hybrid *Glycine max* plants according to claim 1 wherein said harvesting of step (d) is conducted by the use of a combine.

18. An improved process for the efficient production of seeds capable of growing male fertile $F_1$ hybrid *Glycine max* plants according to claim 1 wherein in step (e) said separation of soybean seeds is carried out by use of photoelectric seed-sorting equipment.

19. An improved process for the efficient production of seeds capable of growing male fertile $F_1$ hybrid *Glycine max* plants according to claim 1 wherein following step (e) said substantially uniform assemblage of seeds derived from soybean plants (i) is at least 95 percent pure.

20. An improved process for the efficient production of substantially uniform assemblages of seeds capable of growing male fertile $F_1$ hybrid *Glycine max* plants and seeds capable of growing restorer plants for use in the production of the same comprising:
(a) growing in a planting area a substantially random population of (i) cytoplasmically male sterile soybean plants which form seeds possessing maternally derived homozygous recessive dark-colored seedcoats attributable to the presence of homozygous recessive genes, and (ii) male fertile restorer soybean plants which form seeds possessing maternally-derived seedcoats which are light-colored over at least a portion of their surfaces attributable to the presence of homozygous dominant genes and when crossed with said cytoplasmically male sterile soybean plants enable the formation of seeds on said cytoplasmically male sterile soybean plants which are capable of growing male fertile $F_1$ hybrid soybean plants which upon self-pollination form seeds which substantially uniformly exhibit maternally-derived light-colored seedcoats,
(b) forming pollen on said male fertile restorer soybean plants (ii) which is substantially non-aerodynamic and substantially incapable of being airborne,
(c) crossing said cytoplasmically male sterile soybean plants (i) and said male fertile restorer plants (ii) with the aid of pollen-carrying bees wherein seeds are formed on said soybean plants (i) having maternally-derived dark-colored seedcoats and seeds are formed on said soybean plants (ii) as a result of self-pollination having maternally-derived seedcoats which are light-colored over at least a portion of their surfaces,
(d) harvesting in bulk the seeds formed on said plants (i) and (ii) of said planting area, and
(e) separating the seeds obtained in said harvesting step (d) on the basis of seedcoat color so as to obtain a substantially uniform assemblage of seeds derived from soybean plants (i) which possess dark-colored seedcoats, and are capable of forming $F_1$ hybrid soybean plants which upon self-pollination form $F_2$ seeds which substantially uniformly exhibit maternally-derived light-colored seedcoats thereby enabling the grower to produce a substantially uniform soybean harvest with respect to seedcoat coloration, and to obtain as a result of said separation a substantially uniform assemblage of seeds derived from soybean plants (ii) which are suitable for use in step (a) if said process is repeated.

21. An improved process for the efficient production of seeds capable of growing male fertile $F_1$ hybrid *Glycine max* plants according to claim 20 wherein the flowering period at said planting area for said male fertile restorer soybean plants (ii) commences before the flowering period for said cytoplasmically male sterile soybean plants (i) and ends after the flowering period for said cytoplasmically male sterile soybean plants (ii).

22. An improved process for the efficient production of seeds capable of growing male fertile $F_1$ hybrid *Glycine max* plants according to claim 20 wherein said soybean plants (i) and (ii) are substantially the same height at the time of said cross-pollination of step (c).

23. An improved process for the efficient production of seeds capable of growing male fertile $F_1$ hybrid *Glycine max* plants according to claim 20 wherein said soybean plants (i) and (ii) of step (a) each possess substantially the same flower coloration.

24. An improved process for the efficient production of seeds capable of growing male fertile $F_1$ hybrid *Glycine max* plants according to claim 20 wherein said soybean plants (i) and (ii) of step (a) each possess purple flowers.

25. An improved process for the efficient production of seeds capable of growing male fertile $F_1$ *Glycine max* plants according to claim 20 wherein said male fertile restorer soybean plants (ii) of step (a) are derived from a mutation which occurred in a substantially pure soybean line which normally produces seeds having light-colored seedcoats wherein the seedcoats of the mutant are dark-colored over at least a portion of their surfaces.

26. An improved process for the efficient production of seeds capable of growing male fertile $F_1$ hybrid *Glycine max* plants according to claim 20 wherein in step (a) approximately 75 to 85 percent of the plants present in said substantially random population are cytoplasmically male sterile soybean plants (i) and approximately 15 to 25 percent of the plants are male fertile restorer soybean plants (ii).

27. An improved process for the efficient production of seeds capable of growing male fertile $F_1$ hybrid *Glycine max* plants according to claim 20 wherein said maternally-derived seedcoats of said cytoplasmically male sterile soybean plants (i) of step (a) are black in coloration over substantially all of their surfaces.

28. An improved process for the efficient production of seeds capable of growing male fertile $F_1$ hybrid *Glycine max* plants according to claim 20 wherein said maternally-derived seedcoats of said cytoplasmically male sterile soybean plants (i) of step (a) are brown in coloration over substantially all of their surfaces.

29. An improved process for the efficient production of seeds capable of growing male fertile $F_1$ hybrid *Glycine max* plants according to claim 20 wherein said maternally-derived seedcoats of said cytoplasmically male sterile soybean plants (i) of step (a) possess dark-colored saddle areas adjacent the hila which extend over a portion of their surfaces.

30. An improved process for the efficient production of seeds capable of growing male fertile $F_1$ hybrid *Glycine max* plants according to claim 29 wherein said dark-colored saddle areas are black in coloration.

31. An improved process for the efficient production of seeds capable of growing male fertile $F_1$ hybrid *Glycine max* plants according to claim 29 wherein said dark-colored saddle areas are brown in coloration.

32. An improved process for the efficient production of seeds capable of growing male fertile $F_1$ hybrid *Glycine max* plants according to claim 20 wherein said maternally-derived seedcoats of said male fertile restorer soybean plants (ii) of step (a) are yellow in coloration over substantially all of their surfaces.

33. An improved process for the efficient production of seeds capable of growing male fertile $F_1$ hybrid *Glycine max* plants according to claim 20 wherein in step (c) said pollen-carrying bees are primarily honeybees.

34. An improved process for the efficient production of seeds capable of growing male fertile $F_1$ hybrid *Glycine max* plants according to claim 20 wherein honeybee hives are provided in pollinating proximity to said planting area of step (a) at a rate of at least 2 hives per acre of said substantially random population of soybean plants (i) and (ii).

35. An improved process for the efficient production of seeds capable of growing male fertile $F_1$ hybrid *Glycine max* plants according to claim 20 wherein a supplemental pollen source for said pollen-carrying bees is provided in addition to the pollen formed on said male fertile restorer soybean plants (ii) in order to provide ample pollen to support said pollen-carrying bees.

36. An improved process for the efficient production of seeds capable of growing male fertile $F_1$ hybrid *Glycine max* plants according to claim 20 wherein said harvesting of step (d) is conducted by the use of a combine.

37. An improved process for the efficient production of seeds capable of growing male fertile $F_1$ hybrid *Glycine max* plants according to claim 20 wherein in step (e) said separation of soybean seeds is carried out by use of photoelectric seed-sorting equipment.

38. An improved process for the efficient production of seeds capable of growing male fertile $F_1$ hybrid *Glycine max* plants according to claim 20 wherein following step (e) said substantially uniform assemblage of seeds derived from soybean plants (i) is at least 95 percent pure.

39. An improved process for the efficient production of substantially uniform assemblages of seeds capable of growing male fertile $F_1$ hybrid *Glycine max* plants and seeds capable of growing restorer plants for use in the production of the same comprising:
  (a) growing in a planting area a substantially random population of (i) approximately 75 to 85 percent cytoplasmically male sterile soybean plants which form seeds possessing maternally-derived homozygous dominant yellow-colored seedcoats attributable to the presence of homozygous dominant genes, and (ii) approximately 15 to 25 percent male fertile restorer soybean plants which form seeds possessing maternally-derived seedcoats which are black-colored over substantially all of their surfaces attributable to the presence of homozygous recessive genes and when crossed with said cytoplasmically male sterile soybean plants enable the formation of seeds on said cytoplasmically male sterile soybean plants which are capable of growing male fertile $F_1$ hybrid soybean plants which upon self-pollination form seeds which substantially uniformly exhibit maternally-derived yellow-colored seedcoats,
  (b) forming pollen on said male fertile restorer soybean plants (ii) which is substantially non-aerodynamic and substantially incapable of being airborne,
  (c) crossing said cytoplasmically male sterile soybean plants (i) and said male fertile restorer soybean plants (ii) with the aid of honeybees wherein seeds are formed on said soybean plants (i) having maternally-derived yellow-colored seedcoats and seeds are formed on said soybean plants (ii) as a result of self-pollination having maternally-derived seedcoats which are black-colored over substantially all of their surfaces,
  (d) harvesting in bulk by use of a combine the seeds formed on said soybean plants (i) and (ii) of said planting area, and
  (e) separating by use of photoelectric seed-sorting equipment the seeds obtained in said harvesting step (d) on the basis of seedcoat color so as to obtain a substantially uniform assemblage of seeds of at least 95 percent purity derived from soybean plants (i) which possess yellow-colored seedcoats, and are capable of forming $F_1$ hybrid soybean plants which upon self-pollination form $F_2$ seeds which substantially uniformly exhibit maternally-derived yellow-colored seedcoats thereby enabling the grower to produce a substantially uniform soybean harvest with respect to seedcoat coloration, and to obtain as a result of said separation a substantially uniform assemblage of seeds derived from soybean plants (ii) which are capable of growing male fertile restorer soybean plants suitable for use in step (a) if said process is repeated.

40. An improved process for the efficient production of seeds capable of growing male fertile $F_1$ hybrid *Glycine max* plants according to claim 39 wherein the flowering period at said planting area for said male fertile restorer soybean plants (ii) commences before the flowering period for said cytoplasmically male sterile soybean plants (i) and ends after the flowering period for said cytoplasmically male sterile soybean plants (ii).

41. An improved process for the efficient production of seeds capable of growing male fertile $F_1$ hybrid *Glycine max* plants according to claim 39 wherein said soybean plants (i) and (ii) are substantially the same height at the time of said cross-pollination of step (c).

42. An improved process for the efficient production of seeds capable of growing male fertile $F_1$ hybrid *Glycine max* plants according to claim 39 wherein said soybean plants (i) and (ii) of step (a) each possess substantially the same flower coloration.

43. An improved process for the efficient production of seeds capable of growing male fertile $F_1$ hybrid *Glycine max* plants according to claim 39 wherein said soybean plants (i) and (ii) of step (a) each possess purple flowers.

44. An improved process for the efficient production of seeds capable of growing male fertile $F_1$ *Glycine max* plants according to claim 39 wherein said male fertile restorer soybean plants (ii) of step (a) are derived from a mutation which occurred in a substantially pure soybean line which normally produces seeds having light-colored seedcoats wherein the seedcoats of the mutant are black-colored over substantially all of their surfaces.

45. An improved process for the efficient production of seeds capable of growing male fertile $F_1$ hybrid *Glycine max* plants according to claim 39 wherein honeybee hives are provided in pollinating proximity to said planting area of step (a) at a rate of at least 2 hives per acre of said substantially random population of soybean plants (i) and (ii).

46. An improved process for the efficient production of seeds capable of growing male fertile $F_1$ hybrid *Glycine max* plants according to claim 39 wherein a supplemental pollen source for said honeybees is provided in addition to the pollen formed on said male fertile restorer soybean plants (ii) in order to provide ample pollen to support said honeybees.

47. An improved process for the efficient production of seeds capable of growing male fertile $F_1$ hybrid *Glycine max* plants according to claim 39 wherein following step (e) said substantially uniform assemblage of seeds derived from soybean plants (i) is at least 99 percent pure.

48. An improved process for the efficient production of substantially uniform assemblages of seeds capable of growing male fertile $F_1$ hybrid *Glycine max* plants and seeds capable of growing restorer plants for use in the production of the same comprising:

(a) growing in a planting area a substantially random population of (i) approximately 75 to 85 percent cytoplasmically male sterile soybean plants which form seeds possessing maternally derived homozygous dominant yellow-colored seedcoats attributable to the presence of homozygous dominant genes, and (ii) approximately 15 to 25 percent male fertile restorer soybean plants which form seeds possessing maternally-derived seedcoats which are brown-colored over substantially all of their surfaces attributable to the presence of homozygous recessive genes and when crossed with said cytoplasmically male sterile soybean plants enable the formation of seeds on said cytoplasmically male sterile soybean plants which are capable of growing male fertile $F_1$ hybrid soybean plants which upon self-pollination form seeds which substantially uniformly exhibit maternally-derived yellow-colored seedcoats, (b) forming pollen on said male fertile restorer soybean plants (ii) which is substantially non-aerodynamic and substantially incapable of being airborne, (c) crossing said cytoplasmically male sterile soybean plants (i) and said male fertile restorer soybean plants (ii) with the aid of honeybees wherein seeds are formed on said soybean plants (i) having maternally-derived yellow-colored seedcoats and seeds are formed on said soybean plants (ii) as a result of self-pollination having maternally-derived seedcoats which are brown-colored over substantially all of their surfaces, (d) harvesting in bulk by use of a combine the seeds formed on said soybean plants (i) and (ii) of said planting area, and (e) separating by use of photoelectric seed-sorting equipment the seeds obtained in said harvesting step (d) on the basis of seedcoat color so as to obtain a substantially uniform assemblage of seeds of at least 95 percent purity derived from soybean plants (i) which possess yellow-colored seedcoats, and are capable of forming $F_1$ hybrid soybean plants which upon self-pollination form $F_2$ seeds which substantially uniformly exhibit maternally-derived yellow-colored seedcoats thereby enabling the grower to produce a substantially uniform soybean harvest with respect to seedcoat coloration, and to obtain as a result of said separation a substantially uniform assemblage of seeds derived from soybean plants (ii) which are capable of growing male fertile restorer soybean plants suitable for use in step (a) if said process is repeated.

49. An improved process for the efficient production of seeds capable of growing male fertile $F_1$ hybrid *Glycine max* plants according to claim 48 wherein the flowering period at said planting area for said male fertile restorer soybean plants (ii) commences before the flowering period for said cytoplasmically male sterile soybean plants (i) and ends after the flowering period for said cytoplasmically male sterile plants (ii).

50. An improved process for the efficient production of seeds capable of growing male fertile $F_1$ hybrid *Glycine max* plants according to claim 48 wherein said soybean plants (i) and (ii) are substantially the same height at the time of said cross-pollination of step (c).

51. An improved process for the efficient production of seeds capable of growing male fertile $F_1$ hybrid *Glycine max* plants according to claim 48 wherein said soybean plants (i) and (ii) of step (a) each possess substantially the same flower coloration.

52. An improved process for the efficient production of seeds capable of growing male fertile $F_1$ hybrid *Glycine max* plants according to claim 48 wherein said soybean plants (i) and (ii) of step (a) each possess purple flowers.

53. An improved process for the efficient production of seeds capable of growing male fertile $F_1$ *Glycine max* plants according to claim 48 wherein said male fertile restorer soybean plants (ii) of step (a) are derived from a mutation which occurred in a substantially pure soybean line which normally produces seeds having light-colored seedcoats wherein the seedcoats of the mutant are brown-colored over substantially all of their surfaces.

54. An improved process for the efficient production of seeds capable of growing male fertile $F_1$ hybrid *Glycine max* plants according to claim 48 wherein honeybee hives are provided in pollinating proximity to said planting area of step (a) at a rate of at least 2 hives per acre of said substantially random population of soybean plants (i) and (ii).

55. An improved process for the efficient production of seeds capable of growing male fertile $F_1$ hybrid *Glycine max* plants according to claim 48 wherein a supplemental pollen source for said honeybees is provided in addition to the pollen formed on said male fertile restorer soybean plants (ii) in order to provide ample pollen to support said honeybees.

56. An improved process for the efficient production of seeds capable of growing male fertile $F_1$ hybrid *Glycine max* plants according to claim 48 wherein following step (e) said substantially uniform assemblage of seeds derived from soybean plants (i) is at least 99 percent pure.

* * * * *